United States Patent [19]

Nikoonahad

[11] Patent Number: 5,633,747
[45] Date of Patent: May 27, 1997

[54] VARIABLE SPOT-SIZE SCANNING APPARATUS

[75] Inventor: Mehrdad Nikoonahad, Menlo Park, Calif.

[73] Assignee: Tencor Instruments, Milpitas, Calif.

[21] Appl. No.: 361,135

[22] Filed: Dec. 21, 1994

[51] Int. Cl.$^6$ .................................................. G02F 1/33
[52] U.S. Cl. .................... 359/312; 359/305; 359/308; 359/286; 369/54; 369/116; 369/97; 369/121; 356/394; 356/237; 250/234
[58] Field of Search ........................ 359/312, 305, 359/308, 285, 286, 287, 310; 369/54, 116, 97, 44.14, 112, 121; 356/394, 237, 392, 338, 398; 250/234

[56] References Cited

U.S. PATENT DOCUMENTS

| | | | |
|---|---|---|---|
| 3,851,951 | 12/1974 | Eveleth | 359/286 |
| 4,218,142 | 8/1980 | Kryger et al. | |
| 4,441,124 | 4/1984 | Heebner et al. | |
| 4,522,466 | 6/1985 | Lindig et al. | 359/308 |
| 4,556,290 | 12/1985 | Roulot | 350/358 |
| 4,577,932 | 3/1986 | Gelbart | 359/305 |
| 4,601,576 | 7/1986 | Galbraith | 356/237 |
| 4,602,342 | 7/1986 | Gottlieb et al. | 359/308 |
| 4,614,116 | 9/1986 | Huston et al. | 359/286 |
| 4,750,163 | 6/1988 | Yamamiya et al. | 369/54 |
| 4,827,125 | 5/1989 | Goldstein | 250/234 |
| 4,898,471 | 2/1990 | Stonestrom et al. | 356/394 |
| 4,912,487 | 3/1990 | Porter et al. | 346/108 |
| 5,008,851 | 4/1991 | Brandstetter et al. | 359/305 |
| 5,050,156 | 9/1991 | Barton | 369/116 |
| 5,120,136 | 6/1992 | Oakley | 369/97 |
| 5,122,898 | 6/1992 | Picault | 359/298 |
| 5,184,343 | 2/1993 | Johann et al. | 369/116 |
| 5,185,733 | 2/1993 | Finkelstein et al. | 369/54 |
| 5,210,735 | 5/1993 | Hoshino et al. | 369/54 |

FOREIGN PATENT DOCUMENTS 63-285449  11/1988  Japan.

OTHER PUBLICATIONS

Mehrdad Nikoonahad et al., "Pulse Compression Acoustic Microscopy Using SAW Filters", *IEEE Transactions on Sonics and Ultrasonics*, vol. SU-32, No. 2, Mar. 1985, pp. 152–163.

*Primary Examiner*—Loha Ben
*Attorney, Agent, or Firm*—Majestic, Parsons, Siebert & Hsue

[57] ABSTRACT

An apparatus for both deflecting a beam of light illuminating a spot on a surface and varying the size of the spot, electronically, without changing any system components. The apparatus includes an acousto-optic deflector driven with a linear FM signal produced by a chirp signal generator. The linear FM signal is characterized with a dispersion rate, and the chirp signal generator includes a chirp dispersion selector to vary the dispersion rate. A beam of collimated light passes through the acousto-optic deflector and appropriate focusing optics image the beam onto a spot in a nominal focal plane. The chirp dispersion selector sets the dispersion rate in accord to a nominal rate, resulting in the beam illuminating a spot in the focal plane. Generally, the focal plane coincides with a wafer surface, of the type having periodic and non-periodic features on it. The spot size may be varied from that of a diffraction limited spot to a spot whose maximum size is system dependent. The spot size varies as a result of changing the dispersion rate of the chirp signal. The spot size may vary as it is scanned, or may remain fixed during the inspection of a wafer. In this manner, inspection by periodic feature comparison may be implemented when it proves advantageous. Alternatively, a larger spot may be obtained when periodic feature comparison would provide no benefit, and spatial filtering would achieve an enhanced signal/background.

36 Claims, 3 Drawing Sheets

VARIABLE SPOT-SIZE SCANNING APPARATUS

DESCRIPTION

1. Technical Field

The present invention pertains to the field of semiconductor wafer inspection. Specifically, the present invention pertains to a laser scanner for a semiconductor wafer inspection apparatus.

2. Background Art

Monitoring anomalies during the manufacture of integrated circuits or semiconductor wafers is an important factor to increasing production yields. Numerous types of anomalies, for example, pattern defects and particulate contaminants, can occur on a wafer's surface. Ascertaining the presence, location and type of anomaly can aid in determining both at which step in the process the anomaly occurred and whether a wafer should be discarded.

Originally, anomalies were monitored manually by visual inspection of wafer surfaces for the presence of particulate matter. These contaminants, usually dust or microscopic silicon particles, caused many of the defective wafers. However, manual inspection proved time-consuming and unreliable due to operator errors or an operator's inability to observe certain defects. The ever increasing size of the wafer surface, along with the decreasing dimensions of the components thereon, resulted in a sharp increase in the number of components on the wafer's surface. The need for automation became manifest.

To decrease the time required to inspect wafer surfaces, many automatic detection systems were introduced. A substantial majority of these automatic inspection systems detect defects and contamination based on the scattering of light. For example, see U.S. Pat. No. 4,601,576 to L. Galbraith, assigned to the assignee of the present invention.

Another inspection system is disclosed in U.S. Pat. No. 4,912,487 to Porter et al. wherein a system illuminates a target surface with an argon ion laser beam. An acousto-optical deflector is driven with a chirp signal and placed in the path of the beam to cause it to sweep out raster scan lines. The target is placed on a stage capable of bi-directional movement. The beam has an angle of incidence normal to the target and the stage moves so that it is scanned along adjacent contiguous strips of equal width.

In U.S. Pat. No. 4,898,471 to Stonestrom et al., an apparatus and method for detecting particles on a patterned surface is disclosed wherein a single light beam is scanned, at a grazing angle of incidence, across the surface. The surface contains a plurality of identical dies with streets between them. With the beam scanning parallel to the streets, a single channel collection system detects scattered light from an azimuthal angle that maximizes particle signals while reducing pattern signals. A processor constructs templates from the detected light which corresponds to individual dies and then compares the templates to identify particles on the dies.

These aforementioned systems each includes two major components: illumination optics and collection-detection optics. Illumination optics generally consists of a light source producing a beam of light, e.g. a laser, and an apparatus for focusing and scanning the beam. Anomalies present on the wafer's surface scatter incident light. The collection optics detects the scattered light with reference to the known beam position. The scattered light is then converted to electrical impulses which can be measured, counted and displayed as bright spots on an oscilloscope or other monitor.

The sensitivity of the illumination optics is dependent upon the surface of the wafer illuminated. Sensitivity, in this context, is a measure of the signal from an anomaly as compared to the background signal. If the surface illuminated is rough, e.g., a patterned surface, this reduces the sensitivity of the system because such areas produce random scatter which makes it difficult to determine the presence of an anomaly. The random scatter can produce a background signal up to four orders of magnitude larger than the signal from the anomaly. Generally there are two types of patterns: periodic features, e.g. memory arrays, and non-periodic features, e.g. the quasi-random logic, forming a microprocessor.

Under laser illumination, the light scattered from periodic features exhibits a periodic diffraction pattern. This diffraction pattern can be removed by an appropriate spatial filter at a Fourier transform plane, resulting in a high signal/background contrast. Based on the theory of Fourier optics, the size of the diffraction spots are inversely proportional to the size of the illumination spot. Therefore, the larger the illumination spot, the more concentrated the power in the diffraction spots, providing more effective spatial filtering to reduce background signals. With respect to periodic regions, it is evident that the larger the illumination spot, the greater the detection sensitivity.

In the case of quasi-random logic, the pattern is non-periodic resulting in a non-periodic intensity distribution at the Fourier transform plane. In this situation, spatial filtering fails to enhance the signal/background contrast. In quasi-random logic area it is desired to use as small a spot size as possible, while maintaining a desirable throughput, to resolve a maximum number of pattern features. To improve the signal/background contrast, periodic feature comparison is employed where adjacent features are compared. On many devices of interest, both array logic and quasi-random logic are present, resulting in two conflicting requirements for the spot size.

It is an object, therefore, of the present invention to provide a scanning apparatus capable of varying a beam spot size to a plurality of sizes without changing any components of the apparatus.

It is a further object of the present invention to provide a high-speed scanning apparatus that varies a beam spot size during a scan without changing any components in the system.

DISCLOSURE OF THE INVENTION

These objects have been achieved with a laser scanner which varies the beam spot size electronically to a plurality of different spot sizes, with one spot size for random logic and another spot size for periodic features. The scanner features an acousto-optic deflector electronically coupled to both a chirp signal generator and a chirp dispersion selector, with the chirp dispersion selector varying a dispersion rate of the chirp signal in accordance with the presence of periodic and non-periodic features on the surface. A laser beam passes through the acousto-optic deflector. A chirp correction lens is positioned to receive the beam exiting the acousto-optic deflector. The beam passing through the chirp correction lens is incident on a scan lens that defines a focal plane. The scan lens is one focal length away from the center of the acousto-optic deflector, thereby providing a telecentric scan on the surface of the wafer.

In operation, the focal plane generally coincides with a wafer surface, of the type having periodic and non-periodic features on it. When the spot illuminates non-periodic features on the surface, the dispersion selector may fix the dispersion of the chirp signal to a nominal rate. For purposes of this invention, a nominal dispersion rate is defined as the dispersion rate which produces a diffraction limited spot at the focal plane where the surface undergoing inspection is located. When the spot illuminates periodic features, the dispersion selector may vary the dispersion rate from the nominal rate, thereby producing, at the focal plane, a spot with dimensions greater than the dimensions of the diffraction limited spot. The apparatus may operate in two different modes. In a first mode, the size of the spot is fixed throughout the inspection. In a second mode, the size of the spot varies, as it is scanned.

The scanning apparatus can augment an existing wafer inspection. In such a system, the wafer surface, resting on a moveable stage, includes a light source producing a beam directed on a wafer, or the like, at a predefined angle. An acousto-optic deflector is provided to deflect the beam across the surface in a first direction, as a series of lines that are generally normal to the incident beam, while the stage moves in a second direction, perpendicular to the first direction. In this manner the spot scans over the entire surface of the wafer with the light scattering from anomalies present thereon. A suitable light collection system is located so as to optimize the capture of light with optimum contrast between light scattered from the anomalies and that scattered from background.

BEST MODE FOR CARRYING OUT THE INVENTION

Figure 1:
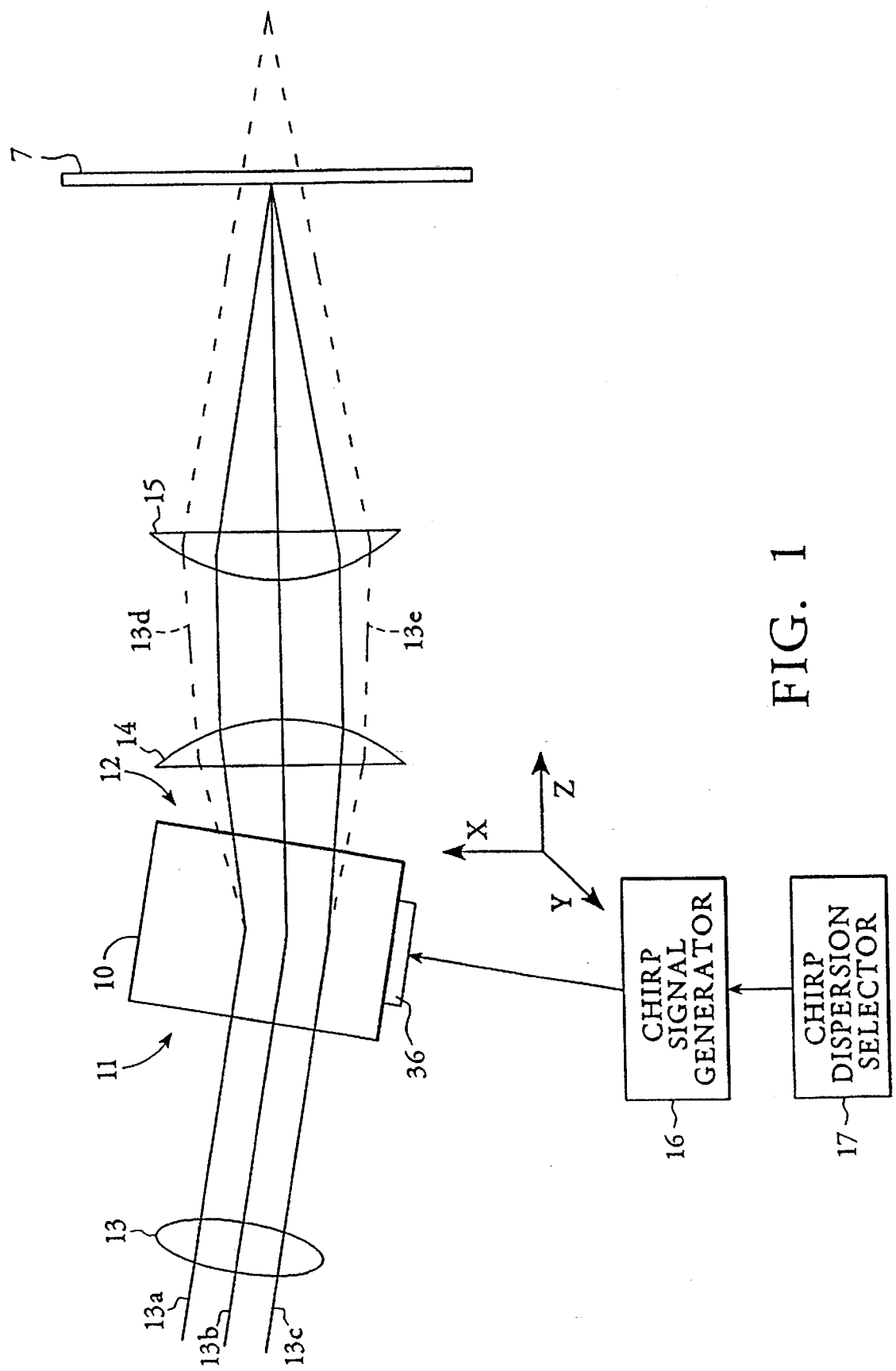
FIG. 1 is a plan view of the present invention showing different divergence of optical outputs at different chirp rates.

With reference to FIG. 1, an acousto-optic deflector (AOD) 10 having an entrance aperture 11 and an exit aperture 12, opposite the entrance aperture 11 is shown with a beam 13, represented by rays 13a–c, passing through it, from the entrance aperture 11 to the exit aperture 12. The AOD 10 may either be a single axis or a dual axis AOD. In the preferred embodiment, beam 13 is collimated. A chirp correction lens 14 is positioned proximate to the exit aperture 12, to receive the beam exiting the AOD 10. A scan lens 15 is positioned one focal length away from the center of the AOD, measured between the entrance 11 and exit apertures 12, and receives the beam 13 passing through the chirp correction lens 14. In this manner, scan lens 15 provides a telecentric scan at nominal focal plane 7. The distance between said center and the chirp correction lens 14 is only a fraction of said focal length. A chirp signal generator 16 is electronically coupled to the AOD 10. The generator 16 drives the AOD 10 with linear FM rf signals: chirp signals.

Each chirp signal is characterized with a dispersion rate. The dispersion rate of the chirp signal μ, is defined as:

$$\mu = \frac{B}{T},$$

where B and T are the chirp bandwidth and time respectively. The chirp signal induces a variable pitch diffraction grating within the AOD 10 causing the rays within beam 13 to be diffracted at different angles. This decollimates the beam passing through the AOD 10, causing the beam at the exit aperture 12 to be uncollimated, i.e., either diverging, shown as rays 13d–e, or converging (not shown). Assume the beam 13 at the entrance aperture 11 is Gaussian in form, at the center of the AOD, the field is defined as follows:

$$u_1(x_1) = u_0 \exp - \left(\frac{2x_1}{W}\right)^2$$

where $u_1(x_1)$ and W are the field amplitude and the full F. width of the beam between the $1/e^2$ points of the intensity distribution. The beam at the exit aperture 12 can then be characterized as follows:

$$u_2(x_2) = u_0 \exp - \left(\frac{2x_1}{W}\right)^2 rect\left(\frac{x_2}{A}\right) expj\left\{\omega_0\left(\frac{x_2}{v}\right) + \frac{1}{2}\mu\left(\frac{x_2}{v}\right)^2\right\}$$

where A is the physical length of the AOD 10 from the entrance aperture 12 to the exit aperture 13, $\omega_0$ is the center frequency of the chirp signal and v is the acoustic velocity in the AOD 10 crystal. The deflection of the beam 13 described by $u_2(x_2)$ is defined as the linear part of the phase. The quadratic part of the phase accounts for the fact that the chirp signal decollimates the beam emerging from the AOD, i.e., the beam at the exit aperture 12 is either converging or diverging. The chirp correction lens 14 is chosen so that it removes the quadratic phase component of $u_2(x_2)$, thereby re-collimating the beam at the exit aperture 12, when the dispersion is set at a nominal dispersion rate. To that end, the chirp correction lens 14 includes an aspherical surface, and it is placed very close to the exit aperture 12, in the manner described above, to reduce the phase distortion in $u_2(x_2)$ due to propagation between them.

Figure 2A:
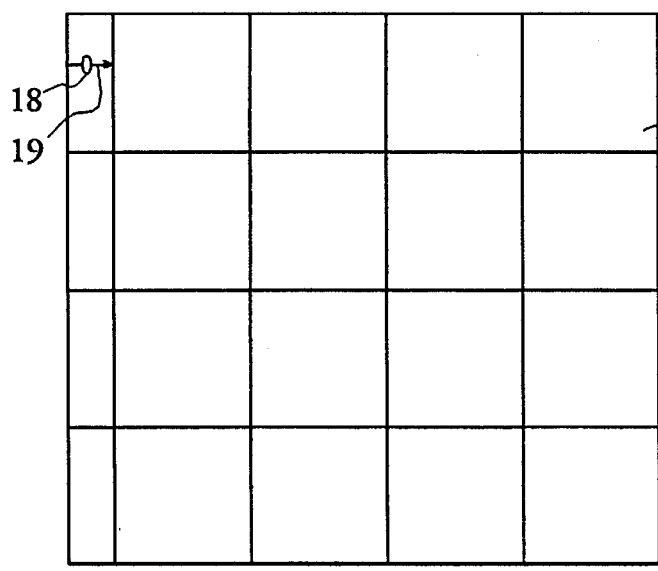
FIG. 2A is a top view of an illuminated spot on a surface having patterned features, traveling along a scan in accord with the present invention.

Referring also to FIG. 2A, at the nominal dispersion rate, the scan lens 15 focuses the beam, collimated by the chirp correction lens 14 having positive cylindrical power, into a spot 18 with a small numerical aperture, defining a nominal spot size. Changing the dispersion rate of the chirp signal, from the nominal rate, increases the spot size/dimension, referred to as the variable spot-size (VSS) effect. To change the dispersion rate, the chirp dispersion selector 17 alters either the chirp sweep time T or bandwidth B. Determining which variable to alter is system dependent. In the preferred embodiment, varying the chirp sweep time T is preferred. Adjusting the chirp bandwidth B results in increasing the length of the scan line.

Either increasing or reducing the dispersion will provide the VSS effect. For a given slope, increasing the dispersion rate causes the beam at the exit aperture 12 to become more divergent and precludes the chirp correction lens 14 from recollimating the entire beam. In this manner, the beam comes to a focus at a longer distance from the nominal focal plane 7. This results in a spot size, larger than the nominal spot size, being present at the nominal focal plane 7. Reducing the dispersion rate of the chirp causes the beam at the exit aperture 12 to become less divergent, again precluding the chirp correction lens from recollimating the entire beam. In this manner, the beam entering the scan lens 15 is converging and comes to focus with a nominal spot size at a shorter distance from the nominal focal plane 7. This also results in a spot size, larger than a nominal spot size, being present at the nominal focal plane. If the slope of the chirp were changed, the VSS effect would still be achieved. The beam exiting the AOD, however, would be convergent, requiring a chirp correction lens having negative cylindrical power to recollimate it.

If a single axis AOD were employed, changing the dispersion rate would change the spot diameter in one direction only: with reference to FIG. 1, the direction would be parallel to the x axis. If a dual axis AOD were employed, changing the dispersion rate would change the spot size in two directions: with reference to FIG. 1, those directions would be parallel to the x axis and parallel to the y axis.

Figure 3:
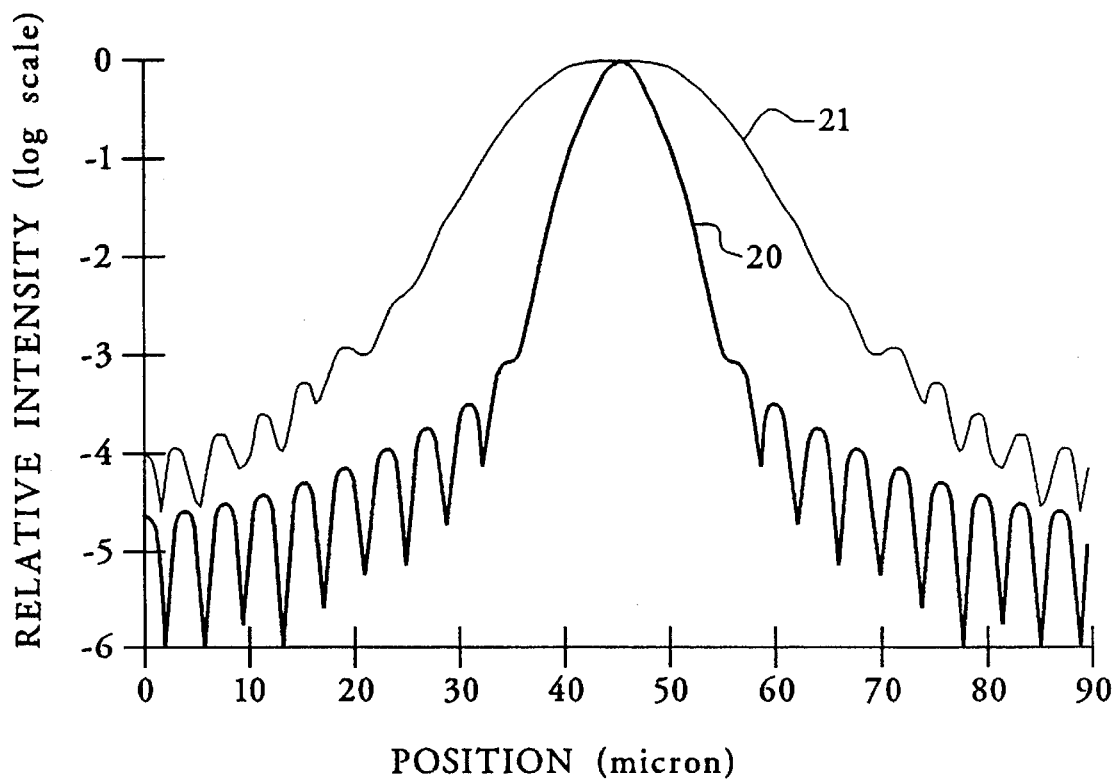
FIG. 3 is a graphical representation of the field distribution of the spot intensity versus position in accord with the present invention.

FIG. 3 is a graphical representation of the VSS effect, showing the intensity distribution at the nominal focal plane. The ordinate, or vertical axis, represents the intensity level of the spot, and the abscissa X represents the position in microns. Assuming the chirp correction lens 14 is a plano-convex lens, the field distribution at the exit aperture of lens 14 is defined as follows:

$$u_3(x_3) = u_2(x_2)\exp\left\{-j2\pi(n-1)\left(\Delta_0 + R\left(1 - \sqrt{1 - \frac{x_3^2}{R^2}}\right)\right)\right\}$$

where n is the refractive index, R is the radius of curvature of the lens and $\Delta_0$ is the center thickness of the lens. Assuming that the field distribution at the focal plane and $u_3(x_3)$ are Fourier transform pairs, the nominal focal plane distribution is defined as follows:

$$u_4(x_4) = \int_{-\infty}^{\infty} u_3(x_3)\exp\left(\frac{-j2\pi x_4 x_3}{\lambda F}\right) dx_3$$

where $\lambda$ and F are the wavelength and focal length of the scan lens respectively. It is seen that using $\lambda$=488 nm, v=0.656 mm/$\mu$s, A=15 mm, W=8.1 mm, F=120 mm, n=1.52238, R=675.67 mm and the dispersion=0.68627 MHz/$\mu$s, line 20 represents a spot having a size, at the 1/$e^2$ points, under 10 microns. Increasing the dispersion to 0.7 MHz/$\mu$s increase the spot size to 27 microns at the 1/$e^2$ points, as represented by line 21.

Figure 4:
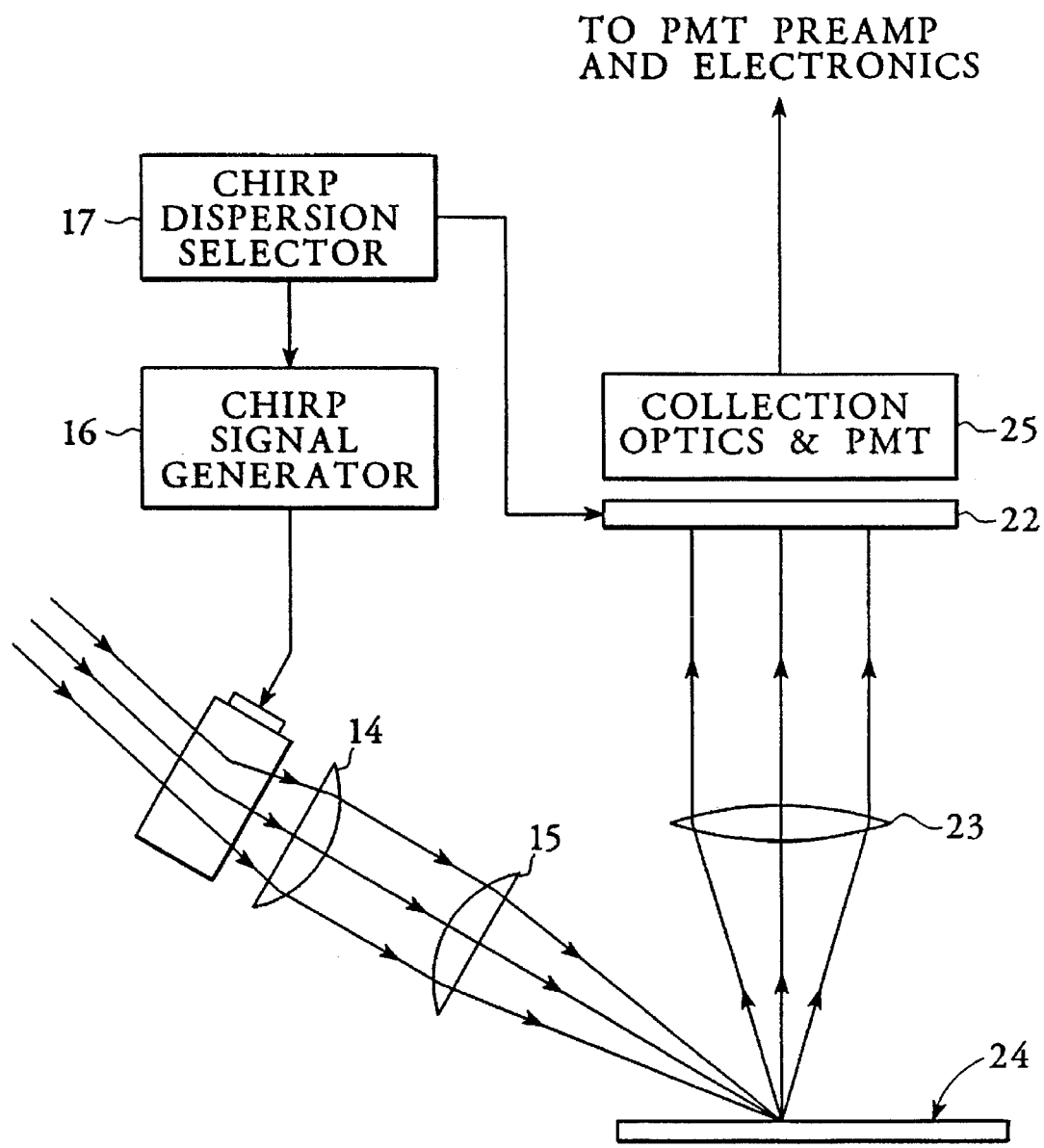
FIG. 4 is a plan view of the present invention incorporated into an inspection system.

Referring to FIG. 4, shown therein is an optical inspection system for defect and foreign matter detection on a surface including the present invention. The chirp dispersion selector is electronically coupled to a programmable spatial filter 22. The Fourier transform lens 23 is positioned to receive light scattered from the wafer surface 24. In this case, the wafer surface 24 is located at the nominal focal plane defined by scan lens 15. The programmable spatial filter 22 is positioned in front of the collection optics 25, which may include a photomultiplier. The collection optics 25 converts the collected light into electrical signals which are further processed by dedicated electronics and finally displayed in various forms, e.g., an image or a template. Although only one collection channel is shown, any number of collection channels may be employed, dependent upon the application.

Figure 2B:
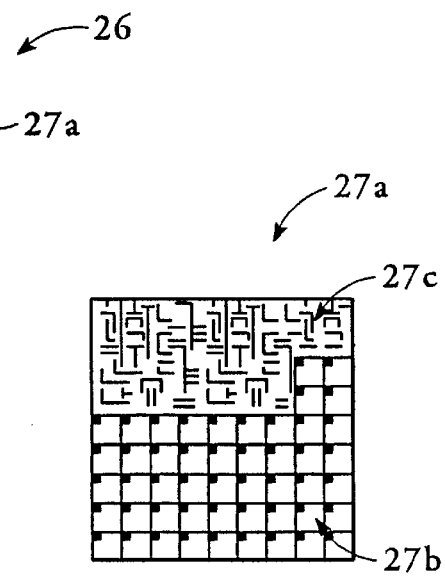
FIG. 2B is a detailed view of a patterned feature of the type having periodic and non-periodic features.

Referring also to FIGS. 2A and 2B, in operation, the topography of the wafer surface 24 is known, either by referencing a map of the surface provided by the manufacturer, or through scanning the surface before inspection. In this manner, the patterned 26 areas of the surface 24 are known. The positions of the periodic 27b and non-periodic 27c features on each die 27a, formed on patterned area 26 are stored in a processor's memory. Generally, a nominal focal plane coincides with the wafer surface 24. The apparatus has at least two modes of operation. In one mode, the dispersion selector fixes the dispersion of the chirp signal in accord with obtaining a desired spot size. In this manner, the dispersion rate of the chirp signal is fixed throughout the entire inspection process of the wafer. For example, if it is desired to inspect for periodic features only, the dispersion selector would be fixed to a dispersion rate that is different from the nominal rate, thereby obtaining a spot size that is larger than a diffraction limited spot size, as described above. This allows inspection by taking advantage of spatial filtering. The entire surface of the wafer would then be scanned so that spot size does not vary during the inspection. If it were desired to detect anomalies in quasi-random logic areas, the dispersion selector would fix the dispersion rate of the chirp signal to the nominal rate. In this manner, periodic feature comparison could be employed. It should be understood that selection of the spot size is not a binary operation. Rather, a range of spot sizes may be obtained by varying the dispersion rate, with the smallest spot size being diffraction limited, and the largest spot size being system dependent.

In a second mode of operation, the apparatus may vary the spot size during the scan of the wafer. In this manner, the chirp dispersion selector 17 varies the dispersion rate of a chirp signal in accord with the presence of periodic 27b and non-periodic 27c features. When the spot illuminates non-periodic features on the surface, the dispersion selector fixes the dispersion of the chirp signal to a nominal rate. This produces a diffraction limited spot at the nominal focal plane, whereby anomaly detection could be achieved with periodic feature comparison. When the spot illuminates periodic features, the dispersion selector varies the dispersion rate from the nominal rate, thereby producing, at the focal plane, a spot having a size larger than the size of the diffraction limited spot. Contemporaneous with the varying of the dispersion rate, a switch, electronically coupled to the chirp dispersion selector 17, activates the programmable spatial filter 22 when the spot illuminates periodic features, and deactivates the spatial filter when the spot illuminates non-periodic features. In this manner, the system detects anomalies by taking advantage of periodic feature comparison. This enables the spot size to vary as it is scanned by the acousto-optic deflector, without changing any mechanical components or introducing new lenses. The spot size may vary in response to the processor's instruction indicating the topography of the wafer surface 24, e.g., whether periodic or non-periodic features are present, at various points along the scan.

I claim:

1. An apparatus for scanning a patterned wafer of the type having periodic and non-periodic features comprising:
   means for providing a beam scanning the surface of a wafer, with a spot; and
   means for varying the dimension of the spot with a first dimension for periodic features and a second dimension for non-periodic features.

2. The apparatus as recited in claim 1 wherein the varying means includes a linear FM signal generator producing a linear FM signal,
   an acousto-optic deflector having an entrance aperture and an exit aperture, opposite the entrance aperture, with beam passing therethrough, the deflector electronically coupled to the generator to receive the linear FM signal, and a chirp dispersion selector, electronically coupled to the deflector, for changing a dispersion rate of the linear FM signal in accord with the presence of periodic and non-periodic features.

3. The apparatus as recited in claim 2 wherein the acousto-optic deflector is a single axis acousto-optic deflector.

4. The apparatus as recited in claim 2 wherein the acousto-optic deflector is a dual axis acousto-optic deflector.

5. The apparatus as recited in claim 2 further including a chirp correction lens positioned proximate to the exit aperture, wherein the beam exiting the acousto-optic deflector is characterized by a quadratic phase component defining a phase curvature and the chirp correction lens includes an aspherical surface to remove the phase curvature in the beam exiting the acousto-optic deflector driven by a nominal dispersion rate.

6. The apparatus as recited in claim 2 wherein the linear FM signal is characterized with a chirp time and chirp bandwidth and the chirp dispersion selector changes the chirp time in accordance with the periodic features on the surfaces.

7. The apparatus as recited in claim 2 wherein the linear FM signal is characterized with a chirp time and chirp bandwidth and the chirp dispersion selector changes the chirp bandwidth in accordance with the periodic features on the surface.

8. An apparatus for deflecting a beam of light illuminating a spot on a surface, of the type having periodic and non-periodic features, comprising:

an acousto-optic deflector having an entrance aperture and an exit aperture, opposite the entrance aperture, a linear FM signal generator electronically coupled to said acousto-optic deflector, a chirp correction lens positioned proximate to said exit aperture, means, electronically coupled to said generator, for varying a dispersion rate of a linear FM signal in accord with the presence of periodic and non-periodic features, wherein the beam passes through the acousto-optic deflector from the entrance aperture to the exit aperture, illuminating a spot on the surface with the size of the spot varying in accordance with the dispersion rate.

9. The apparatus as recited in claim 8 wherein the acousto-optic deflector is a single axis acousto-optic deflector.

10. The apparatus as recited in claim 8 wherein the acousto-optic deflector is a dual axis acousto-optic deflector.

11. The apparatus as recited in claim 8 wherein the dispersion rate is characterized with a chirp time and a chirp bandwidth and said varying means varies the chirp time in accordance with the periodic features on the surface.

12. The apparatus as recited in claim 8 wherein the dispersion rate is characterized with a chirp time and a chirp bandwidth and said varying means varies the chirp bandwidth in accordance with the periodic features on the surface.

13. The apparatus as recited in claim 8 wherein the beam exiting the acousto-optic deflector is characterized by a quadratic phase component defining a phase curvature and the chirp correction lens includes an aspherical surface to remove the phase curvature in the beam exiting the acousto-optic deflector driven by a linear FM signal having a nominal dispersion rate.

14. The apparatus as recited in claim 8 further including a scan lens, defining a focal plane, the scan lens positioned to receive a beam exiting the chirp correction lens, wherein the beam is brought to a diffraction limited focus in the focal plane when the acousto-optic deflector is driven with a linear FM signal having a nominal dispersion rate.

15. The apparatus as recited in claim 14 wherein the chirp correction lens is proximate to the exit aperture, at a distance that is substantially less than the focal length of the scan lens.

16. An optical scanning system for defect and foreign matter detection on a surface comprising, means for producing a beam of light, means for directing the beam onto a sample surface of the type having locations with periodic and non-periodic features, producing an illuminated spot, means for scanning the spot across the sample surface, means for varying the spot size in accord with the locations of the periodic and non-periodic features, and means for detecting light scattered from the surface and generating signals representing the light impinging thereon.

17. The optical scanning system as recited in claim 16 wherein the detecting means is positioned normal to the surface to detect upwardly scattered light.

18. The optical scanning system as recited in claim 17 wherein the detecting means includes a programmable spatial filter and further including a means, in electrical communication with the spatial filter, for activating the spatial filter in accord with the spot illuminating periodic features.

19. The optical scanning system as recited in claim 16 wherein the means for varying the spot size includes an acousto-optic deflector having an entrance and an exit aperture, electronically coupled to both a linear FM signal generator and a chirp dispersion selector, wherein the beam passes through the acousto-optic deflector from the entrance aperture to the exit aperture, and the acousto-optic deflector is driven with a linear FM signal, produced by the generator and characterized by a dispersion rate, the dispersion rate is varied from a nominal rate, by the chirp dispersion selector, in accord with the spot illuminating periodic features to increase the size of the spot and the dispersion is fixed at the nominal rate in accord with the spot illuminating non-periodic features to maintain a nominal spot size.

20. The optical scanning system as recited in claim 19 wherein the means for varying the spot size further comprises a chirp correction lens to collimate a beam exiting the acousto-optic deflector.

21. The optical scanning system as recited in claim 20 wherein the beam exiting the acousto-optic deflector is characterized by a quadratic phase component defining a phase curvature and the chirp correction lens includes an aspherical surface which removes the phase curvature in the beam exiting the acousto-optic deflector driven by a linear FM signal having a nominal dispersion rate.

22. The optical scanning system as recited in claim 20 wherein the dispersion rate is characterized with a chirp time and a chirp bandwidth and the dispersion selector varies the chirp time in accordance with the spot illuminating periodic features on the surface.

23. The optical scanning system as recited in claim 20 wherein the dispersion rate is characterized with a chirp time and a chirp bandwidth and the dispersion selector varies the chirp bandwidth in accordance with the spot illuminating periodic features on the surface.

24. The optical scanning system as recited in claim 20 further including a scan lens, defining a focal plane coinciding with the surface, the scan lens positioned to receive a beam exiting the chirp correction lens, wherein the beam is brought to a diffraction limited focus in the focal plane in accord with illuminating non-periodic features at the focal plane.

25. The optical scanning system as recited in claim 24 wherein the chirp correction lens is proximate to the exit aperture, at a distance that is substantially less than the focal length of the scan lens.

26. A method for scanning a patterned wafer of the type having periodic and non-periodic features comprising:

providing a beam scanning the surface of a wafer with a spot, and varying the dimension of the spot with a first dimension for periodic features and a second dimension for non-periodic features.

27. The method as recited in claim 26 wherein the dimension of the spot is varied electronically.

28. A method for varying a size of a spot produced by a beam of light illuminating a surface comprising the steps of:

providing an acousto-optic deflector, driving the acousto-optic deflector with a linear FM signal, and varying a dispersion rate of the linear FM signal.

29. The method as recited in claim 28 wherein the varying step includes varying a dispersion time.

30. The method as recited in claim 28 wherein the varying step includes varying a dispersion bandwidth.

31. The method as recited in claim 28 wherein the beam exiting the acousto-optic deflector includes a quadratic phase component and further including the step of removing the quadratic component of the beam exiting the deflector.

32. An optical scanning method for anomaly detection on a surface comprising, directing a light beam onto a sample surface to produce an illuminated spot, passing the beam through and supplying a chirp signal to an acousto-optic deflector in order to scan the spot across the sample surface, and providing a control electrical signal for controlling the spot size by altering a dispersion rate of the chirp signal.

33. A method for scanning a patterned surface of the type having periodicity characteristics, comprising:

providing a light beam to illuminate the surface at a spot, scanning the beam to cause the spot to move across the surface, and varying a dimension of the spot with the periodicity characteristics of the surface.

34. The method of claim 33, wherein said scanning step includes supplying a chirp signal to an acousto-optic deflector, and wherein said varying step alters a dispersion rate of the chirp signal.

35. An apparatus for deflecting a beam of light illuminating a spot on a surface, comprising:

an acousto-optic deflector, a chirp signal generator supplying a chirp signal to said acousto-optic deflector, means for varying a dispersion rate of the chirp signal.

36. The apparatus of claim 35, further comprising a chirp correction lens positioned proximate to said deflector.

* * * * *